(12) United States Patent
Huber et al.

(10) Patent No.: US 8,684,002 B2
(45) Date of Patent: Apr. 1, 2014

(54) DEVICE FOR FLOW RATE LIMITATION AT LOW DIFFERENTIAL PRESSURES

(75) Inventors: Martin Huber, Egenhofen (DE); Tobias Kolb, München (DE); Bernhard Müllinger, München (DE)

(73) Assignee: Activaero GmbH, Gemunden (DE)

( * ) Notice: Subject to any disclaimer, the term of this patent is extended or adjusted under 35 U.S.C. 154(b) by 597 days.

(21) Appl. No.: 12/849,482

(22) Filed: Aug. 3, 2010

(65) Prior Publication Data

US 2011/0030682 A1 Feb. 10, 2011

(30) Foreign Application Priority Data

Aug. 6, 2009 (EP) .................................... 09167361

(51) Int. Cl.
*A61M 15/00* (2006.01)
(52) U.S. Cl.
USPC ............ 128/205.24; 128/200.24; 128/204.18
(58) Field of Classification Search
None
See application file for complete search history.

(56) References Cited

U.S. PATENT DOCUMENTS

| | | | | |
|---|---|---|---|---|
| 3,995,625 A * | 12/1976 | Needham | ................. | 128/204.26 |
| 6,070,573 A * | 6/2000 | Howe et al. | ............. | 128/200.14 |
| 6,401,710 B1 | 6/2002 | Scheuch | | |
| 6,463,929 B1 | 10/2002 | Scheuch | | |
| 6,571,791 B2 | 6/2003 | Scheuch | | |
| 6,681,762 B1 * | 1/2004 | Scheuch et al. | ........... | 128/200.14 |
| 7,464,704 B2 * | 12/2008 | Braithwaite | ............. | 128/200.21 |
| 7,891,358 B2 | 2/2011 | Kolb | | |
| 2002/0017293 A1 * | 2/2002 | Scheuch et al. | .......... | 128/200.22 |
| 2002/0078951 A1 * | 6/2002 | Nichols et al. | .......... | 128/200.22 |
| 2002/0078955 A1 * | 6/2002 | Nichols et al. | ........... | 128/203.26 |
| 2009/0056708 A1 * | 3/2009 | Stenzler et al. | .......... | 128/200.14 |

FOREIGN PATENT DOCUMENTS

| | | | | |
|---|---|---|---|---|
| DE | A-100 29 119 | 6/2000 | | |
| DE | A-199 12 461 | 9/2000 | | |
| DK | WO2006042547 | * 4/2006 | ............ | A61M 16/08 |
| EP | B-0 050 654 | 5/1981 | | |
| EP | A-0 965 355 | 2/1999 | | |
| EP | A-1 036 569 | 3/2000 | | |
| EP | A-1 136 921 | 2/2001 | | |

* cited by examiner

*Primary Examiner* — Jackie Ho
*Assistant Examiner* — Eric Bryant
(74) *Attorney, Agent, or Firm* — Kagan Binder, PLLC

(57) ABSTRACT

A device for the flow rate limitation at low differential pressures, in particular for the limitation of the inhalation volume flow during the inhalation of therapeutic aerosols, comprising a housing with at least an inlet opening, at least an outlet opening and a flow channel arranged therebetween, wherein the flow channel is restricted by a flexible wall extending along the flow channel, characterized in that the flexible wall has a control area of less than 100 mm$^2$.

19 Claims, 5 Drawing Sheets

B-B

DEVICE FOR FLOW RATE LIMITATION AT LOW DIFFERENTIAL PRESSURES

CROSS-REFERENCES TO RELATED APPLICATION

This application claims priority to European Application No. 09 16 7361.6, filed Aug. 6, 2009, which is incorporated herein by reference in its entirety.

TECHNICAL FIELD

The invention relates to a device for flow rate limitation at low differential pressures, in particular for limitation of the inhalation volume flow during the inhalation of therapeutic aerosols or of dosed pharmaceuticals in the form of aerosol into the lungs, or inhaled or exhaled breathing gases. Suitable pharmaceuticals include analgesics, anti-angina agents, anti-allergics, antihistamines and anti-inflammatory agents, expectorants, antitussives, bronchodilators, diuretics, anti-cholinergics, corticoids, xanthins, antitumor agents, therapeutically active proteins or peptides such as insulin or interferon, antioxidants, anti-inflammatory substances, active ingredients or drugs as well as combinations thereof.

BACKGROUND

The administration of pharmaceuticals for treating respiratory diseases, such as asthma, as well as agents for the prophylactic treatment and treatment of mucous membranes of the tracheobronchial tract is preferred. The administration of corticoids is possible here.

The variable flow rate limitation in lung diagnosis apparatuses is a further preferred field of application. This is possible for all measurement methods using, e.g., aerosol particles for the diagnosis.

DE-A-199 12 461 discloses a device for limiting the flow at low differential pressures, particularly for limiting the inhalation flow volume during the inhalation of therapeutic aerosols. The device consists of a housing including an inhalation opening, an exhalation opening and a flow channel arranged therebetween, said flow channel having a flat, oblong cross-section with flexible large-surface walls. Depending on the differential pressure between the exhalation opening and the inhalation opening and the flexibility of the wall material, the cross-section of the flow channel can be reduced in size to suit a predetermined maximum inhalation flow volume.

The administration of pharmaceuticals in the form of an aerosol to the lungs by inhalation is essentially influenced by four factors: (i) the particle size and particle properties of the aerosol; (ii) the breathing volume of the patient; (iii) the patient's breathing flow; and (iv) the patient's morphometry and respiratory system. Whereas aerosols in suitable particle sizes have been produced by conventional systems, the parameters "breathing volume" and "breathing flow" (rate of breathing) are taken into account either insufficiently or not at all. This leads to an uncontrolled inhalation of the aerosol, which in turn leads to the fact that an insufficient amount of aerosol particles reaches the lungs or does not reach the areas to be treated (e.g., alveolar area) within the lungs.

EP-A-0 965 355 discloses a device for controlled inhalational administration of controlled-dosage drugs into the lungs. Said controlled inhalator comprises a closed recipient adapted to be charged with a predeterminable aerosol volume and from which the aerosol may be withdrawn via a control means for controlling the inhalation flow. Said control means of this known inhalator is either an adjustable valve or a critical nozzle. The breathing flow can be limited by using an adjustable valve or a critical nozzle.

EP-B-0 050 654 discloses an inhalation apparatus for administering pulmonary medication. Said inhalation apparatus comprises an inflatable envelope from which aerosol can be inhaled through a mouthpiece. This aerosol is introduced via a nebuliser into the inflatable envelope from a cartridge prior to inhalation. The mouthpiece has a restriction to limit the amount of air flowing through the mouthpiece during inhalation. This restriction limits the breathing flow during inhalation.

The two mentioned inhalation devices are characterized in that there is a flow rate limitation, i.e., during the inspiratory phase the breathing flow increases only slowly and the increase in breathing flow decreases constantly, leading to a constant flattening of the curve in the graph of the breathing flow vs. time. This flow rate limitation leads to the fact that, depending on the patient's inspiratory capacity, the breathing flow increases differently up to a maximum flow value. Thus, the flow is nearly kept at a constant level. This means that in the known inhalators, the intended flow rate limitation may lead to a more constant aerosol deposition in the lungs.

EP-A-1 036 569 discloses a method of and a device for providing a constant medicament dose for an inhalational administration at a low inhalation flow rate. This device consists of a closed container reducible in terms of volume, a mouthpiece connected to the container, on which a powder-aerosol generator can be connected for availability of the aerosol, a housing reducible in terms of volume, which surrounds the container on all sides and from which the mouthpiece is led out in sealed form, and means for controlling the inlet and outlet of air into or out from the zone between the container and the housing. The housing is adapted to be changed from a volume compression condition into an envisaged expanded availability condition for creating the envisaged aerosol volume in the container.

Furthermore, DE-A-100 29 119 discloses a device for the flow limitation at low differential pressures, in particular for the limitation of the inhalation volume flow during the inhalation of therapeutic aerosols. This device consists of a housing with at least an inlet opening, at least an outlet opening and a flow channel with at least a flexible wall arranged therebetween, whose cross-section is reducible to a predetermined size for a predetermined maximum inhalation volume flow depending on the negative pressure prevailing between the inhalation and exhalation openings and the flexibility of the wall material.

EP-A-1 163 921 discloses an inhalation device with a self-expanding container for a predetermined aerosol volume, means for introducing aerosol from an aerosol dispenser into the container and control means for controlling the inhalation flow. The control means keeps the inhalation flow at an essentially constant level during the entire aerosol inhalation period, wherein the control means comprises four flow channels which are radially arranged between a central inlet opening and outlet openings which are radially spaced apart from the inlet opening. The four radial flow channels are formed by four radially arranged, rectangular ribs extending from an essentially rigid wall to an essentially flexible wall, wherein one rib is longer than the others.

It is important regarding the intended administering of pharmaceuticals in the field of aerosol therapy that a certain inhalation volume flow is not exceeded. At the same time the patient's work of breathing at the inhalation device should be as little as possible. This means that during inspiration the patient should not have to create a great negative pressure so that the inhalation can also be performed by patients with bad lung function. In order to ensure the mobility of the patients, especially inhalators for administering emergency pharmaceuticals such as, e.g., fast acting beta-2-sympathomimetica, have to be administered with small handy inhalation devices. Prior art systems, however, could not integrate a breathing flow control in hand-held units due to the big dimensions of the flow rate limitation valves. Conventional dosed aerosol inhalation systems, be it for fluid or dry powder aerosols, exhibit a compact design, mostly operable with one hand. Such inhalation systems have no device to prevent the negative effect of a too high air flow on a good active ingredient deposition. An intended volume flow limitation during inhalation of therapeutic aerosols cannot be achieved in hand-held devices.

SUMMARY

It is an object of the present invention to provide a miniaturised device for flow rate limitation at low differential pressures for the use in hand-held devices, where the functional parameters remain constant or are even improved. This object is achieved with a device comprising the features of the claims.

The device for the flow rate limitation at low differential pressures according to the invention, in particular for the limitation of the inhalation volume flow during the inhalation of therapeutic aerosols, comprises, according to a first aspect, a housing with at least an inlet opening, at least an outlet opening and a flow channel arranged therebetween. The flow channel is restricted by a flexible wall extending along the flow channel. Furthermore, the flexible wall has a control area A of less than 100 mm$^2$. In the present invention the control area A is said area or partial area of the flexible wall which contributes to the control section of the flow limiter. This is the base area of the variable flow channel, reduced by the area of the inlet opening and the outlet opening. It is the area of the flow channel influencing the control, i.e., the "active" area. Preferably, the control area A is smaller than 75 mm$^2$, more preferably smaller than 15 mm$^2$.

In flow direction, the flow channel has a planar elongate cross-section a×b, formed by the flexible wall, a wall opposing the flexible wall, and two cross walls. This cross-sectional area is preferably smaller than 15 mm$^2$. The height b of the flow channel is maximally 3 mm, preferably less than 2 mm. In the neutral or initial state, the cross-section a×b is constant along the length of the flow channel. The at least one flexible wall reduces the cross-section of the flow channel through the negative pressure in the flow channel created during inhalation of the aerosol. Thus, no dynamic pressure or pressure drop is created. The flow rate limitation device according to the invention is preferably formed such that a differential pressure of less than 30 mbar, preferably less than 10 mbar, depending on the size of the flow channel, is required for achieving a gas flow rate of maximum 30 l/min, preferably 12 l/min.

According to the invention, the shortest distance between inlet opening and outlet opening is smaller than 10 mm, preferably smaller than 5 mm, more preferably about 1.5 mm. The entire flow rate limitation device preferably has an overall outside length of less than 25 mm, preferably less than 22 mm, and has a width of maximally 15 mm, preferably maximally 12 mm. The entire height is preferably maximally 7 mm, preferably 4 mm. According to the invention, and in view of such dimensions, an inhalation flow of 30 l/min is achieved at a differential pressure of less than 30 mbar at the mouthpiece of the inhalation device. Preferably, a flow of 12 l/min at less than 10 mbar is also possible, depending on the size of the flow channel.

A further preferred characterising feature of the device of the invention is the ratio of control area A of the flow channel to the cross-section periphery (corresponding to 2×a+2×b) of the controlling, i.e., active flow channel in neutral state. This ratio is preferably less than 2, more preferably less than 1.4. A further preferred characterising feature of the device of the invention is the ratio of control area A of the flow channel to periphery U of the control area in neutral state. This ratio is preferably less than 2, more preferably less than 1 and most preferably less than 0.7. A ratio in this area enables a low pressure drop in the flow channel. Thus, the invention considerably differs from the prior art by its reduction in length and width of the base area of the variable flow channel at concurrently significantly reduced area-periphery ratio.

Moreover, according to a preferred embodiment, the ratio between the cross-sectional area of inhalation or exhalation opening to the control area A of the flexible wall is smaller 5 to 1, preferably smaller 3 to 1, and bigger 1 to 1.

Moreover, according to a preferred embodiment, the ratio of control area A of the flow channel to cross-section (a×b) of the flow channel in neutral state, i.e., without applied differential pressure, is less than 3, preferably less than 2.

Up to a differential pressure of 30 mbar, the flow rate limitation behavior of the device of the invention exhibits a hysteresis graph, which, at falling differential pressure values, differs maximally 20% from the growth curve at rising differential pressures. More preferably, the deviation is maximally 10%, most preferably maximally 5%.

In unstressed condition, the flexible wall has a distance of more than 1 mm and less than 3 mm, preferably less than 2 mm and more preferably about 1.7 mm, from the opposite side. The distance determines the maximum flow value. Moreover, the flexible wall has a thickness of preferably 0.05 to 0.3 mm, more preferably of 0.1 to 0.2 mm, and most preferably of 0.15 mm. The thickness of the flexible wall is thus considerably smaller than the height of the flow channel. The flexible wall preferably consists of an elastic material and is, more preferably, a silicone membrane or consists of thermoplastic elastomers. The maximum length of the flexible wall is preferably about 25 mm and the maximum width is about 15 mm.

According to a further preferred embodiment, the inlet and/or outlet opening(s) have a chamfer of more than 0.5 and less than 1 mm at the respective edges facing the flow channel. The chamfer can be provided, e.g., in the form of a curve, such as in the form of a quadrant, preferably in a radius of 1 mm. According to the invention, this enables a reduction in the pressure difference since the pressure is better distributed in the flow channel and the pressure gradient is reduced.

The inlet opening and the outlet opening are arranged at opposite ends of the flow channel. Preferably the inlet opening and the outlet opening are arranged perpendicularly to the flow channel. The inlet opening and the outlet opening preferably have a diameter of 5 to 8 mm, more preferably of 6 to 8 mm, 5 to 7 mm, or 6 to 7 mm, most preferably of 6.5 mm. The centre axes of the inlet opening and the outlet opening are arranged at a distance from each other at preferably 8 to 12 mm, more preferably 8 to 11 mm, 8 to 10 mm, 9 to 12 mm, 9 to 11 mm, 10 to 12 mm or 10 to 11 mm, most preferably 10 mm.

As explained above, in the neutral, i.e., initial state, the flow channel has a constant rectangular cross-section in flow direction, wherein the width a is large compared to a small height b. In an alternative embodiment, however, the cross-section of the flow channel, in flow direction and without applied differential pressure, i.e., in the neutral or initial state, is not constant. Rather, the flow channel cross-section exhibits a minimum at a place where the flow channel cross-section enlarges upstream and/or downstream. This minimum is already present in the neutral state of the flow rate limitation device, i.e., it cannot be compared or mixed up with a minimum resulting from a negative pressure acting on the flow limiter and bending of the membrane. Particularly preferably, an enlarging cross-section is present both upstream and downstream. Preferably, the minimum is in the middle of the length of the channel. However, the invention also covers the alternative of an eccentric position of the minimum. Thus, in this embodiment, the height b increases from the minimum to the inlet or outlet opening. The area of the first and second housing components facing the flow channel are convexly formed in flow direction. However, according to the invention, only the wall of the first housing component at which the flexible mat abuts is convex, whereas the opposite wall of the second housing component is still planar.

A merely laminar flow and higher flow speed are achieved with this expanding cross-section of the flow channel. Thus, the control behavior is further improved.

It is further preferred that the flow channel cross-section is not constant transversely to the flow direction, i.e., in width direction a, but exhibits a minimum, preferably in the middle and at least the area of the first housing component is convex also in width direction.

Moreover, the invention comprises a hand-held inhalation device with a flow rate limitation device according to the invention.

The compact design of the flow rate limitation device of the invention now enables a flow rate control in inhalation systems which could not have been equipped with such systems due to their sizes. The laminar, flexible membrane and significantly reduced control area enable very small sizes of the flow rate limitation valve. At the same time a flow control at reduced differential pressures can be obtained by the new arrangement of the inlet and outlet channels. A further positive effect resulting from the reduced design is a reduced hysteresis of the pressure-flow graph. This ensures that the identical flow values are achieved both at increasing and decreasing differential pressures.

The device for the flow rate limitation at low differential pressures according to the invention, in particular for the limitation of the inhalation volume flow during the inhalation of therapeutic aerosols, comprises, according to a second aspect, a housing with at least an inlet opening, at least an outlet opening and a flow channel arranged therebetween. The flow channel is restricted by a flexible wall extending along the flow channel. The device according to the invention further provides an inhalation flow of 30 l/min at a differential pressure of less than 30 mbar at the mouthpiece of the inhalation device. Preferably, a flow of 12 l/min at less than 10 mbar, depending on the size of the flow channel, is also possible.

The device for the flow rate limitation at low differential pressures according to the invention, in particular for the limitation of the inhalation volume flow during the inhalation of therapeutic aerosols, comprises, according to a third aspect, a housing with at least an inlet opening, at least an outlet opening and a flow channel arranged therebetween. The flow channel is restricted by a flexible wall extending along the flow channel. Further in the device of the invention, the ratio of control area A of the flow channel to the cross-section periphery ($=2 \times a + 2 \times b$) of the controlling, i.e., active flow channel in neutral or initial state is less than 2, preferably less than 1.4.

The device for the flow rate limitation at low differential pressures according to the invention, in particular for the limitation of the inhalation volume flow during the inhalation of therapeutic aerosols, comprises, according to a fourth aspect, a housing with at least an inlet opening, at least an outlet opening and a flow channel arranged therebetween. The flow channel is restricted by a flexible wall extending along the flow channel. Moreover, in the device of the invention, the ratio between the cross-sectional area of inhalation or exhalation opening to the control cross-sectional area of the flexible wall is smaller 5 to 1, preferably smaller 3 to 1, and bigger 1 to 1.

The device for the flow rate limitation at low differential pressures according to the invention, in particular for the limitation of the inhalation volume flow during the inhalation of therapeutic aerosols, comprises, according to a fifth aspect, a housing with at least an inlet opening, at least an outlet opening and a flow channel arranged therebetween. The flow channel is restricted by a flexible wall extending along the flow channel. Moreover, according to the device of the invention, the ratio of control area A of the flow channel to cross-section (i.e., $a \times b$) of the flow channel in neutral state, i.e., without applied differential pressure, is less than 3, preferably less than 2.

The device for the flow rate limitation at low differential pressures according to the invention, in particular for the limitation of the inhalation volume flow during the inhalation of therapeutic aerosols, comprises, according to a sixth aspect, a housing with at least an inlet opening, at least an outlet opening and a flow channel arranged therebetween. The flow channel is restricted by a flexible wall extending along the flow channel. In unstressed condition, the flexible wall has a distance of more than 1 mm and less than 3 mm, preferably less than 2 mm and more preferably about 1.7 mm, from the opposite side. The distance determines the maximum flow value.

The device for the flow rate limitation at low differential pressures according to the invention, in particular for the limitation of the inhalation volume flow during the inhalation of therapeutic aerosols, comprises, according to a seventh aspect, a housing with at least an inlet opening, at least an outlet opening and a flow channel arranged therebetween. The flow channel is restricted by a flexible wall extending along the flow channel. Further, in the device of the invention, the ratio of control area A of the flow channel to periphery U of the control area in neutral state is preferably less than 2, more preferably less than 1 and most preferably less than 0.7.

The device for the flow rate limitation at low differential pressures according to the invention, in particular for the limitation of the inhalation volume flow during the inhalation of therapeutic aerosols, comprises, according to an eighth aspect, a housing with at least an inlet opening, at least an outlet opening and a flow channel arranged therebetween. The flow channel is restricted by a flexible wall extending along the flow channel. The flow channel cross-section exhibits in flow direction a minimum in the neutral or initial state.

According to the invention, the preferred embodiments described above in connection with the first aspect of the invention are also to be understood individually and/or in combination as preferred embodiments for the described second to eighth aspects of the invention.

BRIEF DESCRIPTION ON THE DRAWINGS

The invention is described in further detail in the following on the basis of the attached drawings.

FIG. 1b shows a longitudinal section along A-A of FIG. 1a;

FIG. 1c shows a cross-section along B-B of FIG. 1a;

DETAILED DESCRIPTION

Figure 1A:
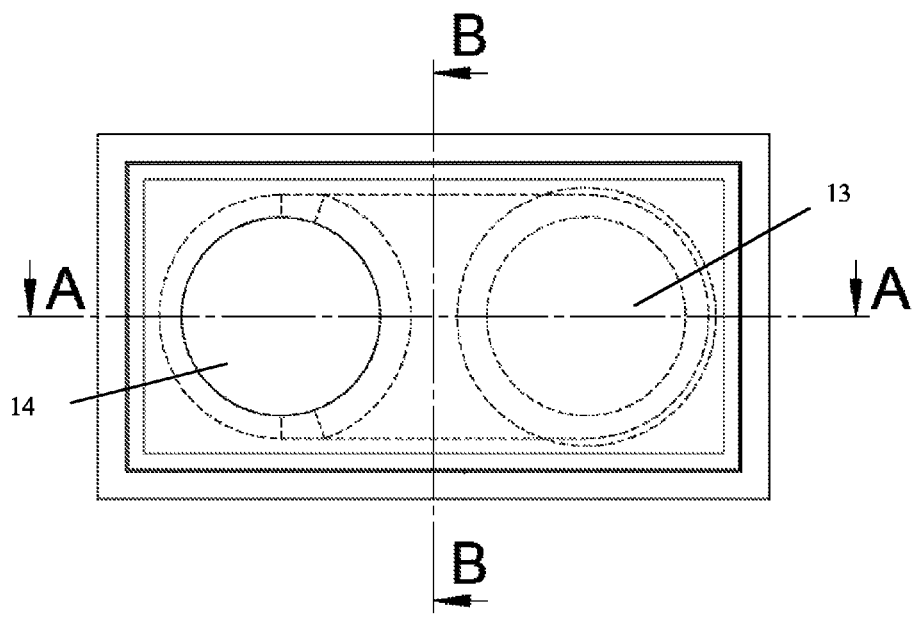
FIG. 1a shows a schematic top view of a flow rate limitation device of the invention according to a preferred embodiment.
Figure 1B:
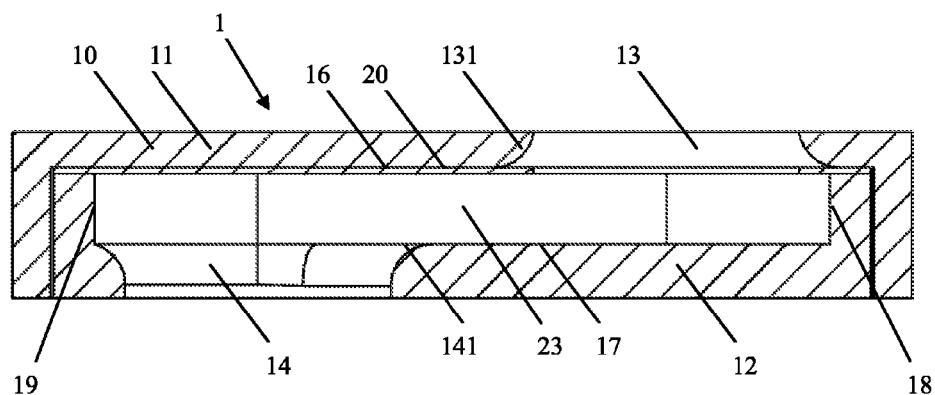
Figure 1C:
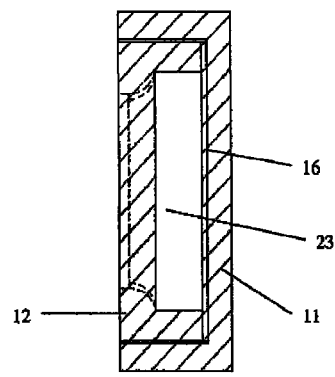

FIGS. 1a to 1c show a preferred embodiment of the flow rate limitation device of the invention from three different views. As is particularly evident from FIG. 1b, the flow rate limitation device 1 consists of a housing 10 comprising a first housing part 11 and a second housing part 12. The housing 10 is preferably elongate and for example cuboidal and is made, e.g., of plastics. The first housing part 11 has a recess into which the second housing part 12 is inserted. The second housing part 12 in turn exhibits a recess which, in assembled state of the housing 10, forms a flow channel 23. In the shown example, the recess in the second housing part has approximately the shape of a "0" (in FIG. 1b of a horizontal "0") with two parallel walls in the middle area, which are respectively connected left and right by a semicircular wall.

However, the assembly of the housing of two separate components is only exemplarily shown in the present case. The invention also comprises housing forms which do not consist of two separate components but are integrally formed of two portions connected with a folding mechanism. Thus, the two portions can be manufactured, e.g., in one process step, e.g., in an injection-moulding process. Alternatively, the housing of the inhalator can already be a part of the flow limiter housing.

An inlet opening 13 is provided in the first housing component 11. In the preferred embodiment, said opening is circular, as is evident from FIG. 1a. However, the invention also comprises embodiments, where several inlet openings are provided, as well as inlet openings of other cross-sectional shapes (e.g., oval or polygonal). The second housing component 12, however, comprises an outlet opening 14. Here, too, with regard to the outlet opening, several openings may be provided, which do not necessarily have to exhibit a circular cross-section. Still, a circular cross-section is preferred for both the inlet opening and the outlet opening. It is further preferred that exactly one inlet opening and exactly one outlet opening are provided.

In the preferred embodiment, a flexible membrane 16 of, e.g., silicone or thermoplastic elastomers, is inserted between the first housing component 11 and the second housing component 12. As is evident from FIG. 1b, the partial area of the membrane 16 shown on the left in the Figure planely abuts the downwards facing wall of the first housing component 11. In the area of the inlet opening 13, the membrane 16, too, exhibits a corresponding opening to enable an air flow from the inlet opening 13 via the flow channel 23 to the outlet opening 14. Alternatively, the flexible wall can also be injection-moulded to the housing component, e.g., by means of a two-component injection-moulding process. The membrane can be injection-moulded, e.g., to a front side.

The flow channel 23 between inlet opening 13 and outlet opening 14 is thus formed by the downwards facing wall 20 of the membrane 16 as well as by the wall 17 of the second housing component 12 opposing the membrane 16. Furthermore, the flow channel 23 is restricted by the two side walls 18 and 19. As is shown in FIG. 1c, the flow channel has a rectangular cross-section in flow direction, having a large width a compared to a small height b.

When air is sucked through the outlet opening 14, it flows into the flow channel 23 via the inlet opening 13. Thus, a negative pressure is created due to the flow resistance. Said negative pressure in the flow channel 23 ensures that the membrane 16 bends inwardly and thus restricts the cross-section of the flow channel 23. This partial area of the membrane 16, which leads to a restriction of the flow channel, is considered to be the control area A of the flow limiter of the invention. The greater the negative pressure in the flow channel 23, the greater the bending of the membrane 16. Thus, the cross-section of the flow channel 23 alters depending on the differential pressure between inlet opening 13 and outlet opening 14. Since the volume flow on the other hand depends on the cross-section of the flow channel 23, the change in cross-section leads to a direct control of the volume flow and thus a flow limitation.

Figure 1D:
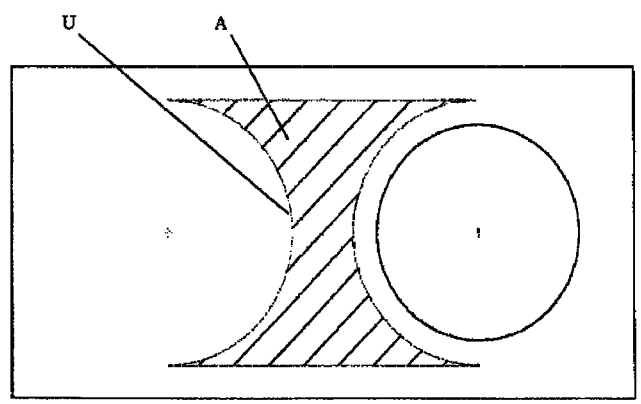
FIG. 1d shows a depiction of the actively controlling area A with its periphery U.

The actively controlling area is again depicted in FIG. 1d, here hatchedly indicated. The periphery U of the actively controlling area consists of the two parallel straight partial sections as well as the two opposing circle segments.

By means of the degressive material flexibility, the force necessary for the bending of the membrane rises with increasing negative pressure in the flow channel up to a boundary value, which determines the desired minimum flow channel cross-section for limitation of the volume flow.

Figure 6:
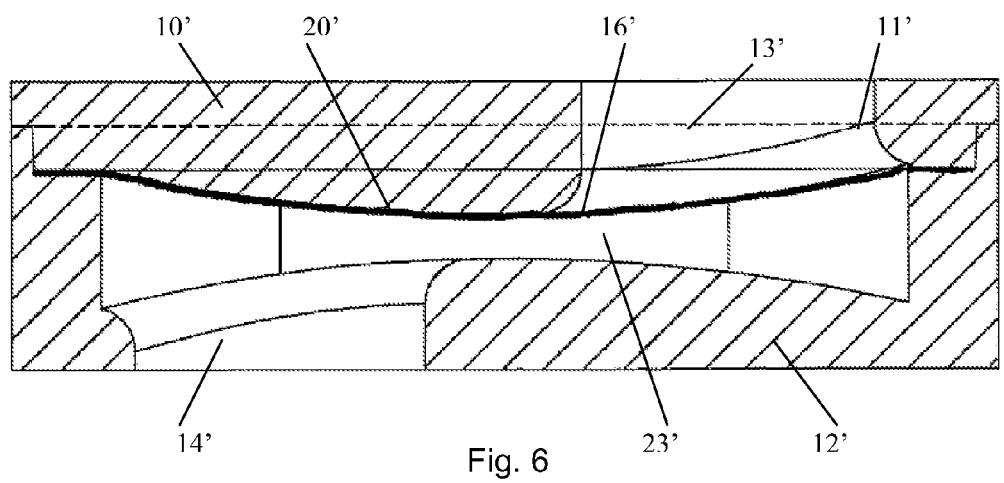
FIG. 6 shows a longitudinal depiction corresponding to FIG. 1b for an alternative embodiment of the invention.

FIG. 6 shows a cross-section of another preferred embodiment of the flow rate limitation device of the invention. This flow rate limitation device 1' consists of a housing 10' comprising a first housing part 11' and a second housing part 12'. The housing is elongate and for example cuboidal. It is made, e.g., of plastics. The first housing part 11' has a recess into which the second housing part 12' is insertable or is inserted. The second housing part 12' in turn exhibits a recess which, in assembled state of the housing 10', forms a flow channel 23'. In the shown example, the recess in the second housing part 12' has, as evident from FIG. 1a for the above-described embodiment, approximately the shape of a "0" (in FIG. 1b of a horizontal "0") with two parallel walls in the middle area, which are respectively connected left and right by a semicircular wall.

The assembly of the housing of two separate components is also only exemplarily shown in this embodiment. The invention also comprises housing forms which do not consist of two separate components but are integrally formed of two portions connected with a folding mechanism. Thus, the two portions can be manufactured, e.g., in one process step, e.g., in an injection-moulding process. Alternatively, the housing of the inhalator can already be a part of the flow limiter housing.

An inlet opening 13' is provided in the first housing component 11'. Said opening is, e.g., circular. However, the invention also comprises embodiments, where several inlet openings are provided, as well as inlet openings of other cross-sectional shapes (e.g., oval or polygonal). The second housing component 12' comprises an outlet opening 14'. Here, too, with regard to the outlet opening, several openings may be provided, which do not necessarily have to exhibit a circular cross-section. Still, a circular cross-section is preferred for both the inlet opening and the outlet opening. It is further preferred that exactly one inlet opening and exactly one outlet opening are provided.

In the preferred embodiment of FIG. 6, a flexible silicone mat 16' is inserted between the first housing component 11' and the second housing component 12'. As is evident from FIG. 6, the partial area of the membrane 16' shown on the left in the Figure planely abuts the downwards facing wall of the first housing component 11'. In the area of the inlet opening 13', the membrane 16', too, exhibits a corresponding opening to enable an air flow from the inlet opening 13' via the flow channel 23' to the outlet opening 14'. In this embodiment, too, the flexible wall can be injection-moulded, as explained above.

The flow channel 23' between inlet opening 13' and outlet opening 14' is thus formed by the downwards facing wall 20' of the membrane 16' as well as by the wall of the second housing component 12' opposing the membrane 16'. Furthermore, the flow channel 23' is restricted by the two side walls 18' and 19'.

As is shown in FIG. 1c, the flow channel of FIG. 6, too, has a basically rectangular cross-section in flow direction, having a large width a compared to a small height b. However, in the embodiment according to FIG. 6, the cross-section of the flow channel is not constant in the neutral state in flow direction. Rather, the flow channel cross-section exhibits a minimum at a place where the flow channel cross-section enlarges upstream and/or downstream. In the example shown in FIG. 6, an enlarging cross-section is present both upstream and downstream. The minimum is in the middle of the length of the channel. The invention also covers the alternative of an excentric position of the minimum. In other words, the height b increases from the minimum to the inlet or outlet opening. The area of the first and second housing components 11' and 12' facing the flow channel are convexly formed as shown in FIG. 6.

When air is sucked through the outlet opening 14', it flows into the flow channel 23' via the inlet opening 13'. Thus, a negative pressure is created due to the flow resistance. Said negative pressure in the flow channel 23' ensures that the membrane 16' bends inwardly and thus restricts the cross-section of the flow channel 23'. This partial area of the membrane 16', which leads to a restriction of the flow channel, is considered to be the control area of the flow limiter of the invention. The greater the negative pressure in the flow channel 23', the greater the bending of the membrane 16'. Thus, the cross-section of the flow channel 23' alters depending on the differential pressure between inlet opening 13' and outlet opening 14'. Since the volume flow on the other hand depends on the cross-section of the flow channel 23', the change in cross-section leads to a direct control of the volume flow and thus a flow rate limitation.

By means of the degressive material flexibility, the force necessary for the bending of the membrane rises with increasing negative pressure in the flow channel up to a boundary value, which determines the desired minimum flow channel cross-section for limitation of the volume flow.

The flow rate limitation device of the invention has, compared to the known prior art flow rate limitation devices, considerably smaller dimensions. Thus, the flow rate limitation device of the invention is smaller by a factor of approximately 5 compared to the flow limitation device of DE-A-100 29 119. According to the invention, however, the flow rate limitation device has not only been reduced in view of its dimensions (downscaling) but rather has been newly designed regarding various parameters in order to maintain at all the functionality in this considerably reduced size. A mere miniaturisation of the known flow rate limitation device would not lead to a functioning flow rate limitation.

The following Table compares an embodiment of the flow rate limitation device of the invention according to FIGS. 1a-1c (right column) with two prior art devices. The flow rate limitation device of DE 199 12 461 is used, e.g., in the inhalation device prototypes of the company Activaero GmbH, Gemuenden, Germany, and the flow rate limitation device known from DE 100 29 119 is known as valve LimiX™ of the company Activaero GmbH, Gemuenden, Germany and is used, e.g., in the inhalation devices of the series Watchhaler™ of the company Activaero GmbH, Gemuenden, Germany.

|  | DE 199 12 461 | DE 100 29 119 | Embodiment of the invention |
|---|---|---|---|
| Areas in mm² | | | |
| Inlet opening | 78.53 | 28.27 | 33.18 |
| Outlet opening | 78.53 | 56.54 | 33.18 |
| Base area membrane | 8320 | 1290 | 200 |
| Base area variable flow channel | 4013.13 | 584.41 | 77.24 |
| Control area A of the flow channel | 3934.6 | 556.14 | 26.98 |
| Cross-section flow channel in neutral state (without differential pressure) | 40 | 98.23 | 13.6 |
| Periphery in mm | | | |
| Periphery membrane in mm | 424 | 127.23 | 60 |
| Periphery U of the control area | 805.96 | 236.73 | 39.58 |
| Cross-section periphery flow channel in neutral state (without differential pressure) | 82 | 85.96 | 19.4 |
| Ratios | | | |
| Cross-section flow channel/cross-section periphery flow channel in neutral state | 0.44 | 0.46 | 0.70 |
| Control area A of the flow channel/cross-section flow channel in neutral state | 98.37 | 5.56 | 1.98 |
| Control area A of the flow channel/periphery U of the control area | 4.88 | 2.35 | 0.68 |

According to the invention, the flow rate limitation device has a control area of less than 100 $mm^2$, in the example shown in the Table of only about 26.98 $mm^2$.

Especially the combination of parameters "control area", the ratio of control area to the periphery of the flow channel in neutral state and chamfer 131, 141 of the edges of the inlet and outlet openings results in a considerably improved mode of operative vis-à-vis known flow rate limitation devices, and this despite the significantly minimized design. This is apparent from FIGS. 2 to 5.

Figure 2:
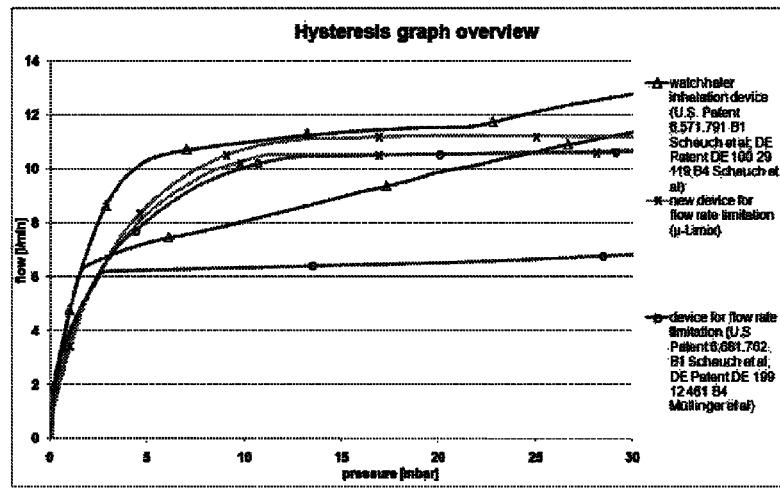
FIG. 2 shows a comparative depiction of the hysteresis graphs of the embodiment of the invention with prior art flow limiters.
Figure 3:
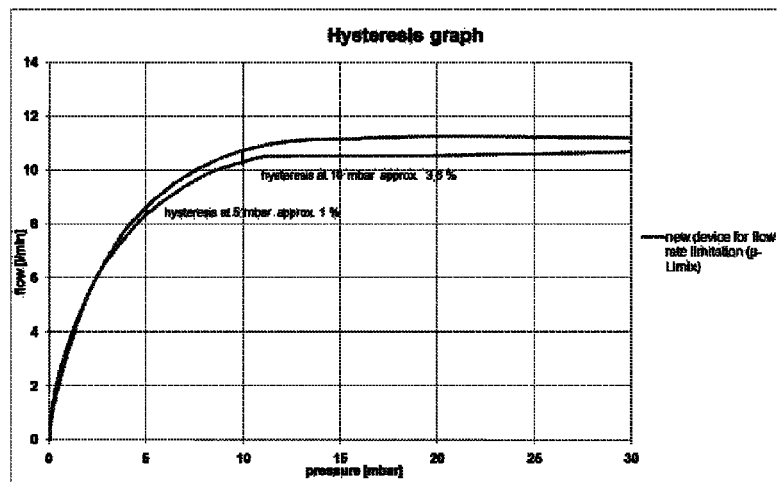
FIGS. 3-5 show the individual curve progressions from FIG. 2.

FIG. 3 shows a hysteresis graph reflecting the flow rate limitation behavior of the flow limiter of the invention according to FIGS. 1*a* to 1*c*. In FIG. 3, as well as in FIGS. 2, 4 and 5, only an area of 0 to 30 mbar is shown, since this is the differential pressure range relevant to the flow rate limitation device of the invention. FIG. 3 clearly reveals that a nearly ideal, very flat hysteresis graph is achieved for the flow rate limitation device of the invention. The growth curve differs by only 1% from the downward curve at a differential pressure of 5 mbar. The difference is only 3.6% at a differential pressure of 10 mbar.

Figure 4:
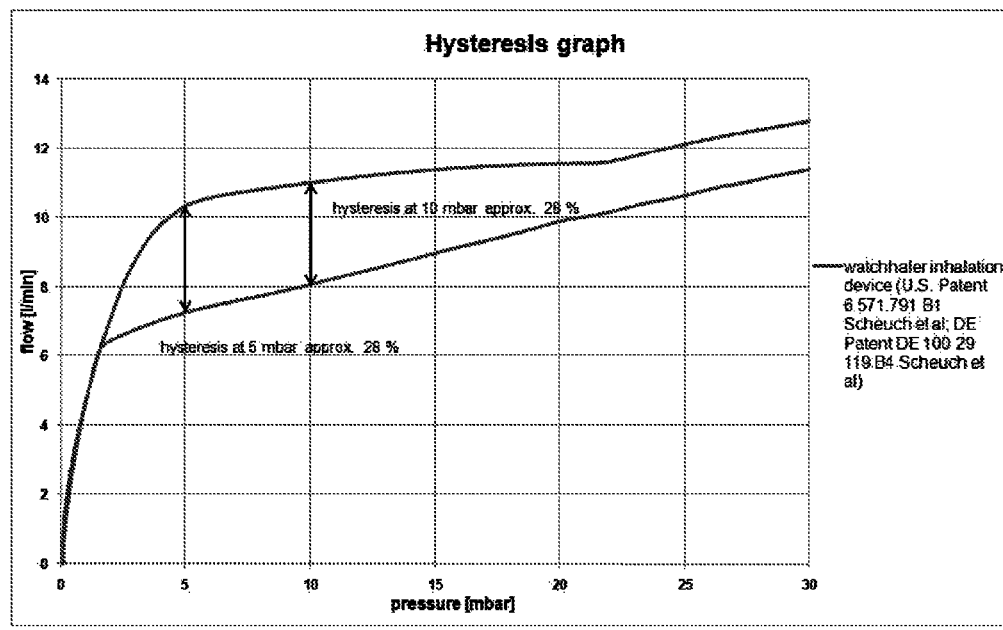

In comparison thereto, FIG. 4 shows the flow rate limitation behavior of the flow limiter known from DE-A-100 29 119. FIG. 4 reveals the considerably more distinct hysteresis, where a difference of about 28% between rising and falling pressure curve ensues at both a differential pressure of 5 mbar and also at 10 mbar.

Figure 5:
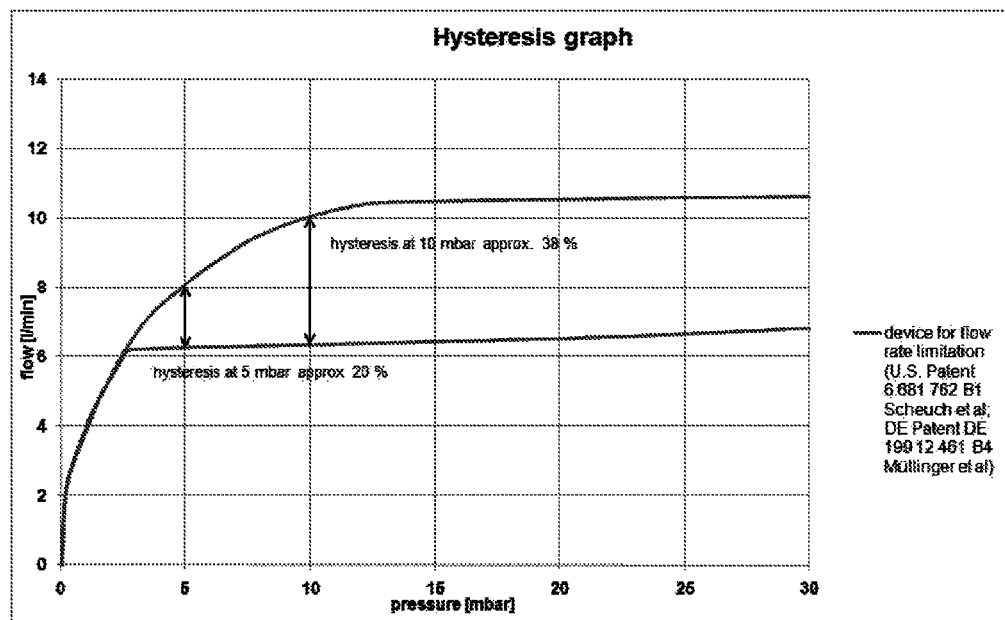

FIG. 5 shows the hysteresis for the flow limiter known from DE-A-199 12 461. Here, too, the hysteresis is significant with a difference of 20% at a differential pressure of 5 mbar and a difference of 38% at a differential pressure of 10 mbar.

The graphs of FIGS. 3 to 5 are again shown in FIG. 2 for a better comparison.

Thus, compared to the known flow limiters, a nearly ideal flow rate limitation behavior is obtained by the flow rate limitation device of the invention.

Although the invention is illustrated and described in detail with the Figures and the corresponding description, said illustration and detailed description are only to be regarded as illustrative and exemplarily and not as being restricting to the invention. Naturally, experts may perform changes and modifications without going beyond the scope of the following claims. In particular, the invention also comprises embodiments with any combination of features which are mentioned or shown above in view of different aspects and/or embodiments.

The invention also comprises individual features in the Figures even if they are shown in connection with other features and/or are not mentioned above.

Furthermore, the term "comprise" and derivations thereof do not exclude other elements or steps. Likewise, the indefinite article "a" and derivations thereof do not exclude a plurality. The functions of several features mentioned in the claims can be fulfilled by a unit. The mere fact that certain dimensions are mentioned in different dependent claims does not mean that a combination of these dimensions cannot be advantageously used. The terms "essentially", "about", "approximately" and the like in connection with a property or a value define in particular exactly the property or the value. All reference signs in the claims are not to be understood as being restricting to the scope of the claims.

We claim:

1. A device for flow rate limitation at low differential pressures, the device comprising: a housing with at least an inlet opening having an area, at least an outlet opening having an area and a flow channel arranged therebetween, the flow channel having a cross-section and a base area; and a flexible wall having a thickness of less than 0.3 mm extending along the flow channel and restricting the cross-section of the flow channel, thereby limiting an inhalation volume flow during inhalation of therapeutic aerosols; wherein the flexible wall has a control area A of less than 100 $mm^2$, wherein the control area A is defined as the base area of the flow channel reduced by the area of the inlet opening and the outlet opening.

2. The device according to claim 1, wherein the flow channel has a planar elongate cross-section and is formed by the flexible wall, a wall opposing the flexible wall, and two cross walls.

3. The device according to claim 2, wherein negative pressure caused by aerosol inhalation through the flow channel causes the at least one flexible wall to reduce the cross-section of the flow channel.

4. The device according to claim 1, wherein the control area is smaller than 75 $mm^2$.

5. The device according to claim 1, wherein the control area is smaller than 50 $mm^2$.

6. The device according to claim 1, the flow channel has a length smaller than 10 mm.

7. The device according to claim 6, wherein the length of the flow channel is smaller than 5 mm.

8. The device according to claim 1, wherein a ratio of the control area A to a cross-section periphery of the flow channel in neutral state is less than 2.

9. The device according to claim 8, wherein the ratio of the control area A to the cross-section periphery of the flow channel in neutral state is less than 1.4.

10. The device according to claim 1, wherein a ratio between a cross-section of the inlet or outlet opening to the control area A is less than 5 to 1 and greater than 1 to 1.

11. The device according to claim 10, wherein the ratio between the cross-section of the inlet or outlet opening to the control area A is less than 3 to 1 and greater than 1 to 1.

12. The device according to claim 1, wherein flow rate limitation properties up to a differential pressure of 30 mbar exhibit a hysteresis graph which, at falling differential pressure values, deviates 20% or less from a growth curve at rising differential pressure values.

13. The device according to claim 12, wherein the deviation is 10% or less.

14. The device according to claim 12, wherein the deviation is 5% or less.

15. The device according to claim 1, wherein, in unstressed condition, the flexible wall has a distance of more than 1 mm and less than 3 mm, from an opposite side of the flow channel.

16. A device for flow rate limitation at low differential pressures, the device comprising: a housing with at least an inlet opening having an area, at least an outlet opening having an area and a flow channel arranged therebetween, the flow channel having a cross-section and a base area; and a flexible wall extending along the flow channel and restricting the cross-section of the flow channel, thereby limiting an inhalation volume flow during inhalation of therapeutic aerosols; wherein the flexible wall has a control area A of less than 100 $mm^2$, wherein the control area A is defined as the base area of the flow channel reduced by the area of the inlet opening and the outlet opening, and wherein the inlet and/or outlet openings have a chamfer of more than 0.5 and less than 1 mm at edges of the inlet and/or outlet openings facing the flow channel.

17. The device according to claim 1, wherein the inlet opening and the outlet opening are arranged at opposite ends of the flow channel.

18. The device according to claim 1, wherein the inlet opening and the outlet opening are arranged perpendicularly to the flow channel.

19. The device according to claim 1, wherein the cross-section of the flow channel in neutral state has a minimum in the flow direction.

* * * * *